(12) United States Patent
Youssefi et al.

(10) Patent No.: US 9,345,620 B2
(45) Date of Patent: May 24, 2016

(54) APPARATUS AND METHOD FOR PROVIDING A LASER SHOT FILE

(76) Inventors: Gerhard Youssefi, Landshut (DE); Ernst Hegels, Kirchheim (DE)

( * ) Notice: Subject to any disclaimer, the term of this patent is extended or adjusted under 35 U.S.C. 154(b) by 630 days.

(21) Appl. No.: 13/098,267

(22) Filed: Apr. 29, 2011

(65) Prior Publication Data

US 2011/0276043 A1 Nov. 10, 2011

Related U.S. Application Data

(63) Continuation of application No. PCT/EP2009/007755, filed on Oct. 29, 2009.

(30) Foreign Application Priority Data

Oct. 30, 2008 (DE) .......................... 10 2008 053 827

(51) Int. Cl.
*A61B 19/00* (2006.01)
*A61F 9/008* (2006.01)

(52) U.S. Cl.
CPC ............. *A61F 9/008* (2013.01); *A61F 9/00806* (2013.01); *A61F 2009/0088* (2013.01); *A61F 2009/00848* (2013.01); *A61F 2009/00857* (2013.01); *A61F 2009/00872* (2013.01); *A61F 2009/00882* (2013.01)

(58) Field of Classification Search
CPC ..... A61F 9/007; A61F 9/008; A61F 9/00802; A61F 9/00825; A61F 2009/0087; A61F 2009/00872; A61F 2009/00878; A61F 2009/0088; A61B 19/00; A61B 19/50; A61B 2019/501; A61B 2019/507
USPC ........ 606/4–6, 10–12; 351/205–212; 623/4.1, 623/5.11–5.16, 6.11–6.15; 128/898
See application file for complete search history.

(56) References Cited

U.S. PATENT DOCUMENTS

| | | | |
|---|---|---|---|
| 5,425,727 A | 6/1995 | Koziol | |
| 5,683,379 A * | 11/1997 | Hohla | ............................... 606/5 |
| 5,740,815 A * | 4/1998 | Alpins | .......................... 128/897 |
| 5,777,719 A | 7/1998 | Williams | |
| 5,891,132 A * | 4/1999 | Hohla | ..................... A61B 19/22 606/10 |
| 5,928,221 A | 7/1999 | Sasnett | |
| 5,949,521 A | 9/1999 | Williams | |
| 5,984,916 A | 11/1999 | Lai | |
| 6,033,075 A | 3/2000 | Fujieda | |
| 6,086,204 A | 7/2000 | Magnante | |
| 6,090,100 A | 7/2000 | Hohla | |
| 6,095,651 A | 8/2000 | Williams | |
| 6,129,722 A * | 10/2000 | Ruiz | ................................. 606/5 |
| 6,132,424 A | 10/2000 | Tang | |
| 6,139,542 A * | 10/2000 | Hohla | .................... A61B 19/22 606/10 |
| 6,159,205 A | 12/2000 | Woodward et al. | |
| 6,271,936 B1 | 8/2001 | Yu et al. | |
| 6,325,792 B1 | 12/2001 | Swinger | |
| 6,332,216 B1 | 12/2001 | Yee | |
| 6,394,999 B1 | 5/2002 | Williams | |
| 6,413,251 B1 * | 7/2002 | Williams | .......................... 606/5 |
| 6,454,761 B1 | 9/2002 | Freedman | |
| 6,500,171 B1 | 12/2002 | Williams | |
| 6,508,812 B1 | 1/2003 | Williams | |
| 6,511,180 B2 | 1/2003 | Guirao et al. | |
| 6,607,521 B2 | 8/2003 | Vinciguerra | |
| 6,635,051 B1 | 10/2003 | Hohla | |
| 6,673,062 B2 * | 1/2004 | Yee et al. | .......................... 606/5 |
| 6,715,877 B2 | 4/2004 | Molebny | |
| 6,755,819 B1 | 6/2004 | Waelti | |
| 6,808,266 B2 | 10/2004 | Youssefi et al. | |
| 6,848,790 B1 | 2/2005 | Dick | |
| 6,923,802 B2 | 8/2005 | Williams | |
| 6,997,555 B2 | 2/2006 | Dick | |
| 7,130,835 B2 * | 10/2006 | Cox | .................... A61F 9/00806 606/4 |
| 7,380,942 B2 | 6/2008 | Molebny | |
| 2002/0026180 A1 | 2/2002 | Nakamura | |
| 2002/0075451 A1 | 6/2002 | Ruiz | |
| 2002/0082629 A1 | 6/2002 | Cox | |
| 2003/0023233 A1 | 1/2003 | Smith et al. | |
| 2003/0048413 A1 | 3/2003 | Ross | |
| 2003/0128335 A1 | 7/2003 | Campin | |
| 2003/0193647 A1 | 10/2003 | Neal | |

(Continued)

FOREIGN PATENT DOCUMENTS

| | | |
|---|---|---|
| DE | 19727573 | 5/1998 |
| DE | 20 2005 018911 | 3/2006 |
| DE | 10 2005 006897 | 8/2006 |
| EP | 0697611 | 2/1996 |
| EP | 1396244 A2 | 3/2004 |
| EP | 1718483 | 11/2006 |
| EP | 1719483 | 11/2006 |
| JP | 2000300596 | 10/2000 |
| JP | 2002524144 | 8/2002 |
| WO | 9527535 | 10/1995 |

(Continued)

OTHER PUBLICATIONS

U.S. 5,423,802, Jun. 13, 1995, Marshall.

(Continued)

*Primary Examiner* — Ahmed Farah
(74) *Attorney, Agent, or Firm* — Thompson Hine LLP

(57) ABSTRACT

The invention relates to an apparatus, an algorithm and a method for providing a laser shot file for use in a laser. The laser may be an excimer laser. The shot file may be applied for performing a refractive laser treatment of an eye or for producing a customized contact lens or an intraocular lens. According to the invention information with respect to a desired ablation profile is provided and a first series of laser shot positions is calculated based on the desired ablation profile. A simulated ablation profile is generated using said first series of laser shot positions and using information about pulse characteristics of a single laser shot. The simulated ablation profile is compared with the desired ablation profile and residual structures are determined.

13 Claims, 15 Drawing Sheets

(56) References Cited

U.S. PATENT DOCUMENTS

| | | |
|---|---|---|
| 2004/0002697 A1 | 1/2004 | Youssefi et al. |
| 2004/0021874 A1 | 2/2004 | Shimmick |
| 2005/0159733 A1 | 7/2005 | Dick |
| 2005/0273088 A1 | 12/2005 | Youssefi |
| 2008/0033408 A1* | 2/2008 | Bueler et al. .................. 606/5 |
| 2008/0058780 A1 | 3/2008 | Vogler |
| 2009/0264874 A1* | 10/2009 | Hegels .................. A61F 9/008 606/5 |

FOREIGN PATENT DOCUMENTS

| | | |
|---|---|---|
| WO | 9611655 | 4/1996 |
| WO | 9848746 | 11/1998 |
| WO | 0124688 | 4/2001 |
| WO | 0128410 A | 4/2001 |
| WO | 0128477 A1 | 4/2001 |
| WO | 0234178 | 5/2002 |
| WO | 03068103 | 8/2003 |
| WO | 03075778 | 9/2003 |
| WO | 2004041104 | 5/2004 |
| WO | 2004052253 A1 | 6/2004 |
| WO | 2004053568 | 6/2004 |
| WO | 2004095187 | 11/2004 |
| WO | 2005007002 | 1/2005 |
| WO | 2007012924 | 2/2007 |
| WO | 2007143111 | 12/2007 |

OTHER PUBLICATIONS

PCT International Search Report regarding U.S. Appl. No. 13/098,267; International Application No. PCT/EP2009/007755; International Filing Date: Oct. 29, 2009; Priority Date: Oct. 30, 2008 for Applicant Technolas Perfect Vision GmbH.

Damien Gatinel, et al., "Three-dimensional representation and qualitative comparisons of the amount of tissue ablation to treat mixed and compound astigmatism," Journal of Cataract and Refractive Surgery, vol. 28 (No. 11), p. 2026-2034 (Nov. 1, 2002).

* cited by examiner

| Zernike Coefficient | Zernike Amplitude |
|---|---|
| Z110 | 0.512 |
| Z111 | -0.063 |
| Z200 | 1.308 |
| Z221 | -0.035 |
| Z220 | 0.399 |
| Z311 | -0.100 |
| Z310 | 0.140 |
| Z331 | 0.044 |
| Z330 | 0.033 |
| Z400 | -0.097 |
| Z420 | -0.021 |
| Z421 | -0.009 |
| Z440 | 0.039 |
| Z441 | -0.044 |
| Z510 | 0.028 |
| Z511 | 0.007 |
| Z530 | -0.001 |
| Z531 | 0.007 |
| Z550 | -0.007 |
| Z551 | 0.000 |

Fig. 1 cross section of ablation in μm cross section of ablation in μm cross section of ablation in μm cross section of ablation in μm cross section of ablation in μm

| Zernike Coefficient | 1st iteration | 2nd iteration |
|---|---:|---:|
| Z110 | 0.112 | -0.004 |
| Z111 | -0.017 | -0.001 |
| Z200 | -0.083 | 0.003 |
| Z221 | -0.004 | 0.001 |
| Z220 | -0.017 | -0.002 |
| Z311 | 0.011 | -0.001 |
| Z310 | 0.046 | 0.001 |
| Z331 | 0.009 | 0.001 |
| Z330 | -0.006 | 0.001 |
| Z400 | -0.001 | -0.004 |
| Z420 | 0.000 | 0.003 |
| Z421 | -0.003 | 0.001 |
| Z440 | 0.001 | -0.004 |
| Z441 | 0.002 | -0.001 |
| Z510 | 0.000 | -0.002 |
| Z511 | -0.002 | -0.001 |
| Z530 | -0.001 | 0.004 |
| Z531 | -0.001 | -0.001 |
| Z550 | 0.000 | 0.003 |
| Z551 | -0.003 | 0.000 |

Fig. 7 cross section of ablation in μm cross section of ablation in μm cross section of ablation in μm cross section of ablation in μm

| Zernike Coefficient | 1st iteration | 2nd iteration |
| --- | --- | --- |
| Z110 | 0.283 | -0.024 |
| Z111 | -0.021 | -0.007 |
| Z200 | -0.266 | -0.002 |
| Z221 | 0.012 | -0.001 |
| Z220 | -0.021 | 0.004 |
| Z311 | 0.035 | 0.003 |
| Z310 | 0.074 | 0.010 |
| Z331 | 0.018 | 0.007 |
| Z330 | -0.005 | -0.002 |
| Z400 | -0.066 | -0.075 |
| Z420 | 0.010 | 0.012 |
| Z421 | 0.012 | 0.015 |
| Z440 | -0.008 | -0.004 |
| Z441 | 0.011 | 0.009 |
| Z510 | -0.035 | -0.029 |
| Z511 | 0.009 | 0.011 |
| Z530 | 0.004 | 0.005 |
| Z531 | -0.004 | -0.005 |
| Z550 | 0.002 | 0.000 |
| Z551 | 0.004 | 0.003 |

Fig. 13

| Zernike – Notation (OSA-standard) | Sight Defect | B&L – Notation |
|---|---|---|
| $Z_0^0$ | piston | Z000 |
| $Z_1^1$ | horizontal tilt | Z110 |
| $Z_1^{-1}$ | vertical tilt | Z111 |
| $Z_2^0$ | defocus | Z200 |
| $Z_2^2$ | 0° astigmatism | Z220 |
| $Z_2^{-2}$ | 45° astigmatism | Z221 |
| $Z_3^1$ | horizontal coma | Z310 |
| $Z_3^{-1}$ | vertical coma | Z311 |
| $Z_3^3$ | horizontal trefoil | Z330 |
| $Z_3^{-3}$ | vertical trefoil | Z331 |
| $Z_4^0$ | spherical aberration | Z400 |
| $Z_4^2$ | secondary 0° | Z420 |
| $Z_4^{-2}$ | secondary 45° | Z421 |
| $Z_4^4$ | horizontal quatrofoil | Z440 |
| $Z_4^{-4}$ | vertical quatrofoil | Z441 |
| $Z_5^1$ | secondary horizontal | Z510 |
| $Z_5^{-1}$ | secondary vertical | Z511 |
| $Z_5^3$ | secondary horizontal | Z530 |
| $Z_5^{-3}$ | secondary vertical | Z531 |
| $Z_5^5$ | horizontal pentafoil | Z550 |
| $Z_5^{-5}$ | vertical pentafoil | Z551 |

Fig. 14

APPARATUS AND METHOD FOR PROVIDING A LASER SHOT FILE

This is continuation of International Application PCT/EP2009/007755, with an international filing date of Oct. 29, 2009, and which claims the benefit of German Application No. 10 2008 053 827.2, with a foreign filing date of Oct. 30, 2008.

FIELD OF INVENTION

The invention relates to an apparatus, a method and an algorithm for providing a laser shot file taking information about the pulse characteristics of an individual laser shot into consideration. The laser shot file may be used for ablating the surface of a cornea in a corneal re-shaping procedure or for producing a customized contact lens or an intraocular lens.

BACKGROUND OF THE INVENTION

Currently used algorithms for providing a laser shot file using finite laser pulse sizes, such as 1 mm or 2 mm, deliver a laser shot file which is an approximation to the intended theoretical ablation profile. This is mainly based on the fact that the used algorithms only use the theoretically total removed volume per pulse, irrespective whether a standard or a customized treatment is planned.

The theoretical ablation profile relates to the desired refractive correction compensating a determined vision error of an eye. The desired refractive correction may be based on diagnostic data obtained by at least one of a subjective refractive error and a measured objective refractive error. The measured refractive error may be obtained by at least one of a wavefront sensor, topographical measurement device or a pachymetry measurement device. Low order aberrations may be determined by a subjective refractive error, e.g. considering the verbal feedback of a patient.

Classical ablation algorithms further induce biodynamic effects which are in general expressed by unintended induced shape aberrations. To compensate for these unintended induced shape aberrations additional ablation of corneal tissue may be necessary, which may cause incremental modifications to the desired ablation profile. Also the fact that the size of pulses, which comprises the pulse diameter, is not infinitely small may cause the need to create a transition zone around the actually relevant central ablation zone.

The final shape of a wavefront may be created by a superposition of known two dimensional surfaces of a known shape. For each of these known shapes a scaling factor may be obtained, e.g. by a software, to get the best representation of the wavefront deformation.

There are various sets of functions which create the already mentioned known two dimensional surfaces. Here in the following the Zernike Polynomial system will be briefly described.

The amplitudes A of Zernike polynomials can be represented mathematically as follows.

$$A_{n,m}^{\pi}$$

Where n represents the Zernike mode, i.e. the main order of the polynomial, which is the primary parameter in the classification of the radial behavior of the polynomial. The parameter n gives more or less the radial distribution. The larger the order n is, the outer in the periphery the major characteristics are located.

The angular characteristic of the polynomial is specified by the parameter m, which describes how often a certain structure is repeated in azimutal direction, i.e. the parameter m gives the azimutal symmetry of the polynomial. The larger the value for m, the more sophisticated the azimutal profile of the polynomial, i.e. the more structures along one azimutal circle can be detected. The parameter $\pi$ describes the symmetry characteristic of the polynomial, i.e., even or odd.

Reference is made to FIG. 15 which illustrates the behavior of a graphical representation of Zernike polynomials with corresponding parameters. The OSA standard notation (Thibos et al., 2000) as used in FIGS. 14 and 15 for the Zernike polynomials Z is defined as follows:

$$Z_n^{\pi \cdot m}$$

The original wavefront error W of the eye can be reconstructed by a linear combination of the calculated Zernike polynomials Z, taking into account their individual amplitudes $A_{n,m}^{\pi}$ using the following equation:

$$W(\rho, \varphi) = \sum_{n,m,\pi} A_{n,m}^{\pi} Z_{n,m}^{\pi}(\rho, \varphi)$$

The notation $Z_{n,m}^{\pi}$ corresponds to $Z_n^{\pi \cdot m}$ of the OSA standard notation. The parameters $\rho$, $\phi$ represent the coordinate values. In the following, the Bausch & Lomb notation (B&L notation) is used.

U.S. Pat. No. 6,090,100 relates to an excimer laser system for correction of vision with reduced thermal effects. It specifically relates to an apparatus and method for controlling the excimer laser system for removing tissue from the eye to perform various types of corrections, such as myopia, hyperopia, and astigmatism correction. In one disclosed embodiment, the excimer laser system provides a relatively large pulse size which provides a relatively large coverage of treatment area per shot. While using such large pulse sizes, the shots are generally not "adjacent" to each other but the pulses overlap to generate the desired degree of ablation at a particular point. For calculating the result of the overlapping pulses, an algorithm is used. In one method of calculating treatment patterns using large, fixed pulse sizes distributed throughout the treatment area, a dithering algorithm is used. Specific reference is made to a rectangular dithering, circular dithering and a line-by-line oriented dithering. Using any variety of shot dithering methods, an array of shots is created for a fixed pulse size spread over a treatment area to correct to the desired degree of ablation. For the respective array, a grid is used with a constant grid width between individual grid positions. With the known dither methods, the shape of the desired ablation profile, which usually is a continuous profile, has to be transferred into a whole-numbered discrete density distribution. Here, the continuous profile represents a planned ablation and the whole-numbered discrete density distribution represents a series of ablating flying spot laser pulses. The residual structure, i.e., the difference between the planned and the achieved profile, has to be minimised. Exact solutions can principally be found numerically but not in a reasonable time. Therefore, for this purpose, dither algorithms are used. The profile is discretised on a given grid. Using a cost function or merit function the algorithm decides for each position of the grid whether to place a shot or not. For this decision, usually only a few neighbouring positions of the grid are taken into account. This dither algorithm saves calculation time without the need that the real size of the pulse is taken into account. It is sufficient to know the volume which is ablated with one laser shot. However, under certain conditions, the known dither algorithms produce artefacts in parts of the profile, e.g., in low-density regions where the next neighbouring shot is too far away. Artefacts may also be produced in high-density regions where at nearly every position, a shot is placed. The positions with no shot also have too large a distance for the assumption that only a few neighbour positions are necessary.

SUMMARY

It is an object of the invention to improve the performance to obtain a laser shot file approximating the theoretical ablation profile up to a predetermined degree. Another object of the invention is to obtain a laser shot file approximating the theoretical ablation profile with lasers having a large range of pulse characteristics, e.g., having different shape and/or size and/or energy distribution over the laser pulse. This range of pulse characteristics may result in a corresponding range of beam profiles. Another object of the invention is to correct high order aberrations of an eye more effectively.

The above objects are achieved by the features of the claims. Aspects of the invention are directed to a method, an algorithm and an apparatus for providing a laser shot file for use in a laser as well as a laser treatment system utilizing the laser shot file. The laser shot file may be used in a laser, e.g. excimer laser for performing a refractive laser treatment of an eye or for producing a customized contact lens or an intraocular lens. The concept of the present invention is based on an iterative processing of the input data for obtaining the approximated laser shot file, which takes information about one or more pulse characteristics of a single laser shot into consideration. Hence, the pulse characteristics for determining a laser shot file is not a theoretical assumption, e.g., only based on the ablated volume per shot. The pulse characteristics of a single laser shot may be obtained by applying independently a single test shot or a series of test shots on a reference material, e.g., once in the lifetime of a laser or after an inspection of a laser, e.g., an excimer laser. The analysis of the effect of the mentioned test shots delivers independently information for one or more pulse characteristics, e.g., the ablation volume. The actual pulse characteristics of the laser shot may also be measured in a certain time interval or before each treatment, before each partial treatment or for checking the beam profile.

In the context of the application, the term "pulse" relates to the spatial distribution of the intensity with a corresponding beam profile and the term "shot" relates to the center position, i.e., the target position of the laser.

Due to the features of the invention it is, inter alia, possible to obtain a laser shot file approximating the theoretical ablation profile with a large range of laser pulse characteristics, e.g., having a different laser pulse size, e.g., diameter. This is advantageous in that a laser having a relatively large pulse size may be employed to ablate relatively small sized structures, i.e. may deliver an ablation profile which is comparable to the results achieved with small sized pulses. Laser pulses having a relatively large size may ablate more tissue per shot and may have a relatively low laser shot repetition rate which may lead to a reduction of the operating time in comparison to laser pulses having a relatively small size. The possibility to employ a laser apparatus having a relatively large pulse size is also advantageous in that existing laser apparatuses may be employed and it is not necessary to use a laser apparatus having a small pulse size.

According to an aspect of the invention, a laser shot profile is provided by calculating a first series of laser shot positions based on a desired ablation profile. The first series of laser shot positions is utilized to generate a simulated ablation profile, wherein in the simulation the actual laser pulse characteristics used for the refractive treatment is taken into consideration. In this way it is possible to assure a high level of accuracy regarding the outcome of a laser treatment as well as a high approximation performance to the desired ablation profile. Due to this feature it is possible to determine a laser shot file for lasers having different pulse characteristics, e.g., ablation volume and/or shape and/or size and/or energy distribution over the laser pulse.

The difference between the simulated ablation profile and the desired ablation profile represented by Zernike coefficients or Seidel aberrations, is determined. A second series of laser shot positions is calculated based on both the desired ablation profile and the residual structures corresponding to the above determined difference. The second series of laser shot positions optimizes the first series of laser shot positions and minimizes the residual structures, at least in an area of interest, which may correspond to a treatment area.

A second simulated ablation profile may be generated using the second series of laser shot positions, which uses information about the pulse characteristics of a single laser shot like the first simulation. The second simulated ablation profile may be compared with the desired ablation profile and residual structures may be determined A further series of laser shot positions based on the desired ablation profile and the determined further residual structures may be calculated and the processing may be iteratively repeated until a certain accuracy is reached, e.g., until the residual structures do not exceed one or more predetermined values.

The residual structure may be filtered, e.g., split into high spatial frequency structures and low spatial frequency structures in order to modify the input for the following calculation to achieve better results. This may be done by expanding the residual structure into Zernike coefficients up to a certain order so that the residual wavefront is created analogical to the original wavefront. The high spatial frequency parts may introduce artefacts in the lower spatial frequency parts due to the iterative calculation. These artefacts may be avoided by assuming that the high spatial frequency parts are good enough because of the limitation by the laser pulse size.

According to an aspect of the invention unintended induced shape aberrations due to biodynamic effects may be compensated when determining the laser shot file. According to a further aspect of the invention a dithering algorithm is utilized when determining at least one of the laser shot positions.

Input data for the method/algorithm/apparatus according to the present invention may be diagnostic data, preferably at least one of a subjective refractive error and a measured refractive error. The measured refractive error may be obtained by at least one of a wavefront sensor, topographical measurement device or a pachymetry measurement device. Low order aberrations, typically understood as being for example the $2^{nd}$ order Zernike type aberrations expressed in sphere, cylinder and related axis, may be determined by a subjective refractive error, e.g. considering the verbal feedback of a patient. High order aberrations, typically understood to be for example $3^{rd}$ and higher order Zernike type aberrations such as coma and trefoil ($3^{rd}$ order) and spherical aberration and secondary astigmatism ($4^{th}$ order), may be determined by measurement means and/or by mathematically given shape change parameters. The mathematically given shape change parameters may represent unintentional vision errors which are induced by a vision correction treatment, such as an induced spherical aberration by an excimer laser ablation process. According to the invention input data may be combined, e.g., to obtain two dimensional maps or matrices based on topography, wavefront or empirical findings.

The output data of the method/algorithm/apparatus according to the present invention may be used to control a laser treatment system for performing a laser vision correction treatment of an eye or for producing a customized contact lens or an intraocular lens.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which:

FIG. 1 shows a table with Zernike coefficients and Zernike amplitudes relating to a wavefront to be corrected for a pupil radius of 2.5 mm;

FIG. 7. shows a table with Zernike coefficients relating to the residual wavefront after the $1^{st}$ and $2^{nd}$ iteration step illustrated in FIGS. 3 to 6;

FIG. 13 shows a table with Zernike coefficients relating to the residual wavefront after the $1^{st}$ and $2^{nd}$ iteration step illustrated in FIGS. 9 to 12;

FIG. 14 shows a map of the Zernike polynomials notation, the respective sight defect and the Bausch & Lomb notation.

DETAILED DESCRIPTION

Figure 2:
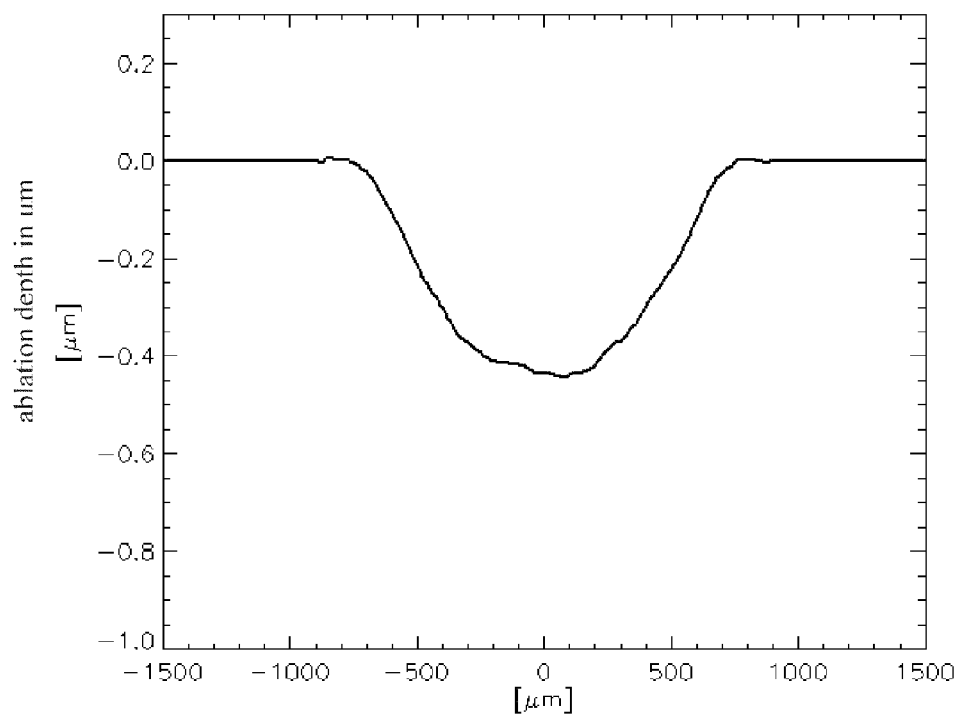
FIG. 2 illustrates a sectional view of a pulse of a single laser shot with a 1.0 mm diameter.
Figure 8:
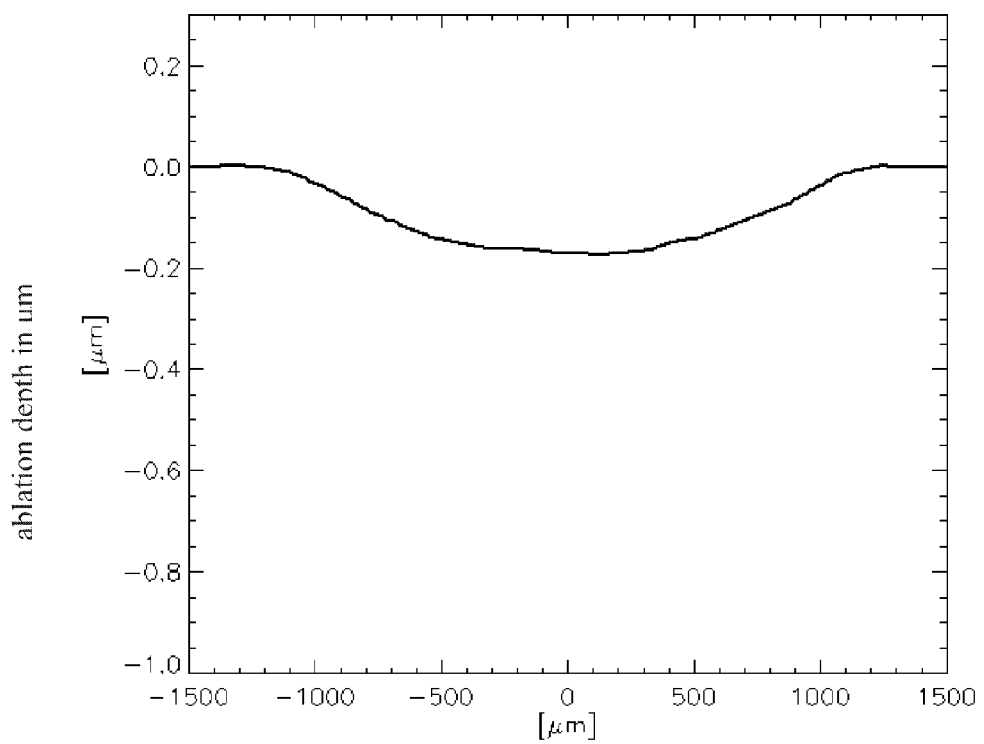
FIG. 8 illustrates a sectional view of a pulse of a single laser shot with a 1.6 mm diameter.

In the following detailed description the invention is explained on the basis of two different laser pulses having a pulse characteristic of a single laser shot as illustrated in FIGS. 2 and 8. FIG. 1 shows an exemplary wavefront to be corrected with the two different laser pulses. The wavefront in FIG. 1 is given in a Zernike notation for a pupil radius of 2.5 mm. Regarding the Zernike coefficients, which are given in the Bausch & Lomb notation (B&L notation) and the respective vision error, reference is made to FIG. 14.

FIG. 2 shows a sectional view of a single laser shot ablation, whereas the laser pulse has a 1.0 mm diameter. More specifically, the ablation depth (y-axis) is shown along a central cross section of the laser pulse. In this example, in the center of the laser pulse which is indicated as 0 μm on the x-axis there is a maximal ablation depth of about 0.4 μm. Every laser may have individual pulse characteristics, e.g. asymmetrical, which may change over the life time of the laser. The pulse characteristics of a single laser shot, such as the ablation, may be measured, e.g., via photo sensitive means or a test shot or a series of test shots in a material which may have at least partially the same characteristics as the material to be ablated based on the obtained laser shot file. In case of refractive eye surgery the test material may be polymethyl methacrylate (PMMA). The pulse caused by this test laser shot is analyzed to obtain the pulse characteristics of the laser, e.g. the laser spot size, shape and energy distribution etc.

Figure 3:
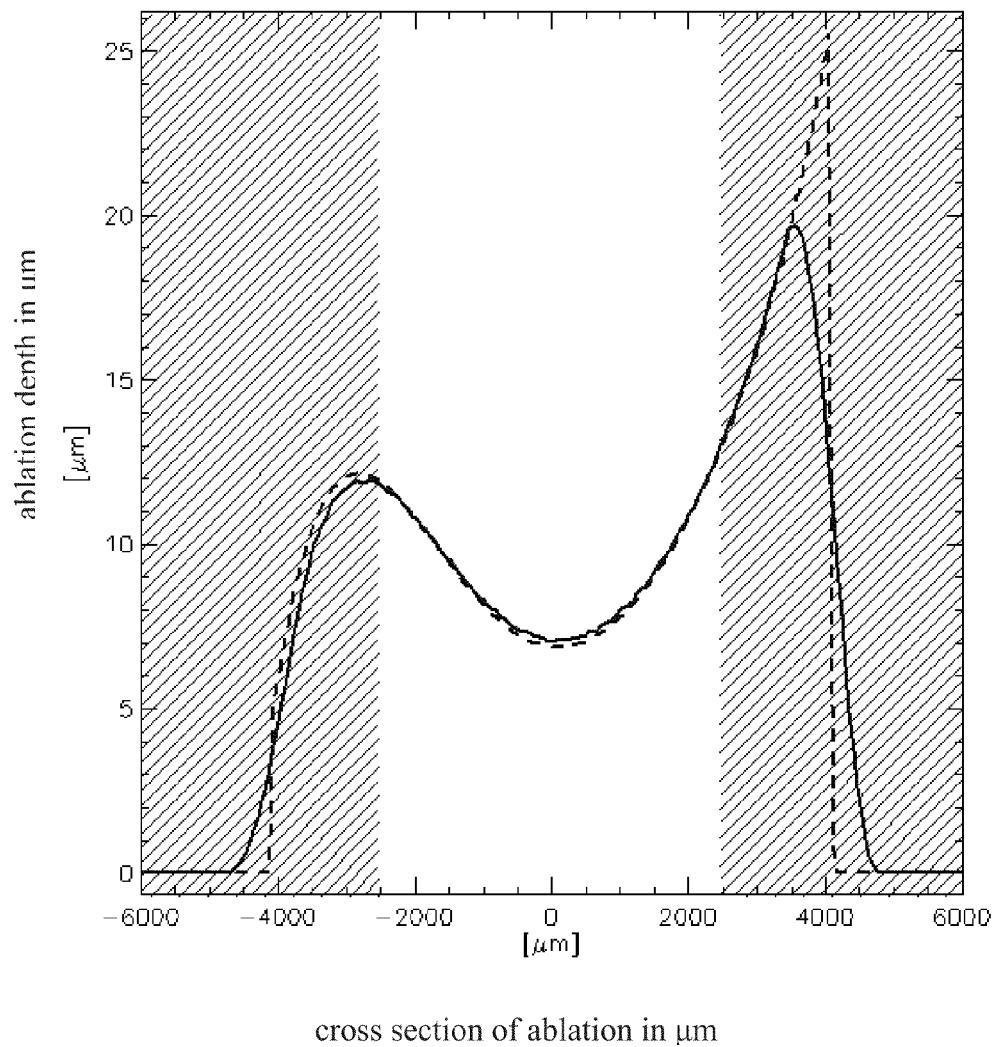
FIG. 3 illustrates a cross section of a simulated ablation profile with the pulse of FIG. 2 in x direction after a $1^{st}$ iteration step.

In FIG. 3 a theoretically determined ablation profile, i.e. a desired ablation profile is illustrated by a dashed line. The x-axis of FIG. 3 relates to the x direction of the cross section of the ablation and the y-axis relates to the ablation depth. The aim of the determination of the laser shot positions is to come as close as possible or at least up to a predetermined degree to the desired ablation profile. According to the invention the determination of the laser shot positions is conducted utilizing information about the actually used laser pulse characteristics of a single laser shot. The non-shaded portion in FIG. 3 relates to the pupil diameter of 5.0 mm, which may be the treatment zone. The data produced in the shaded portion which may represent the transition zone need not be taken into consideration when determining the laser shot positions in the treatment area.

A first series of laser shot positions is calculated based on the desired ablation profile and a simulated ablation profile is generated using said first series of laser shot positions. The first series of laser shot positions may be based on the extrapolated wavefront as described above. In the simulation information about one or more pulse characteristics of a single laser shot as illustrated in FIG. 2 is used. The simulated ablation profile based on the first series of laser shot positions, which corresponds to the $1^{st}$ iteration is illustrated in FIG. 3 by the continuous line. According to the invention, the simulated ablation profile is compared with the desired ablation profile. Based on the comparison residual structures are determined. As can be taken from FIG. 3, the first determination of laser shot positions using information about the pulse characteristics of a single laser shot already provides a result which is quite close to the desired ablation profile in the area of interest, i.e. the pupil area.

The information relating to the wavefront to be corrected may be given as a wavefront of nth-order, e.g. $5^{th}$ order as in FIG. 1, and the first series of laser shot positions may be calculated based on said nth-order wavefront.

Figure 4:
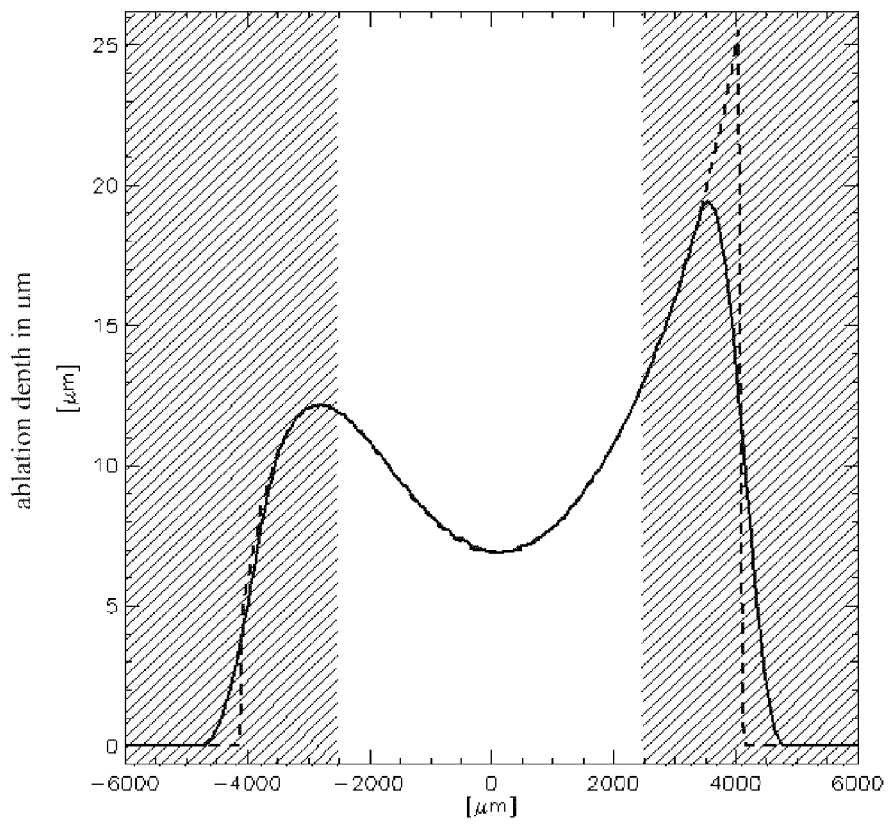
FIG. 4 illustrates the simulated ablation profile of FIG. 3 after a $2^{nd}$ iteration step.

A second series of laser shot positions is calculated based on the desired ablation profile and the determined residual structures for further optimizing the laser shot positions and the corresponding outcome of the laser treatment. A second simulated ablation profile using the second series of laser shot positions may be generated, which is illustrated in FIG. 4. As in FIG. 3, the x-axis relates to the x direction of the cross section of the ablation and the y-axis relates to the ablation depth. The remaining differences between the desired ablation profile and the simulated ablation profile, i.e., the further residual structures may be determined by comparing the second simulated ablation profile with the desired ablation profile. Based on the desired ablation profile and the determined further residual structures a further series of laser shot positions may be calculated.

When determining residual structures based on the comparison of the simulated ablation profile with the desired ablation profile the wavefront of the simulated ablation profile may be added to the wavefront of the desired ablation profile or the Zernike coefficients may be added. The addition of the Zernike coefficients is less complex and may lead to an improved calculation performance.

The above described procedure may be iteratively repeated until a predetermined maximum deviation of the simulated ablation profile to the desired ablation profile, i.e. a certain treatment accuracy, is achieved, wherein the further series of laser shot positions is used as the second series of laser shot positions. In a following iteration the residual wavefront may be added to the previously calculated wavefront.

The difference of the simulated and the desired wavefront may be filtered to obtain low and/or high spatial frequencies by calculating Zernike coefficients up to the order N', wherein in each iteration step a respective N'th order of the Zernike coefficients is used and wherein $$N'=n-2*\text{iteration\_counter}.$$

n is the order of the wavefront information and 'iteration_counter' corresponds to the number of iteration.

Figure 5:
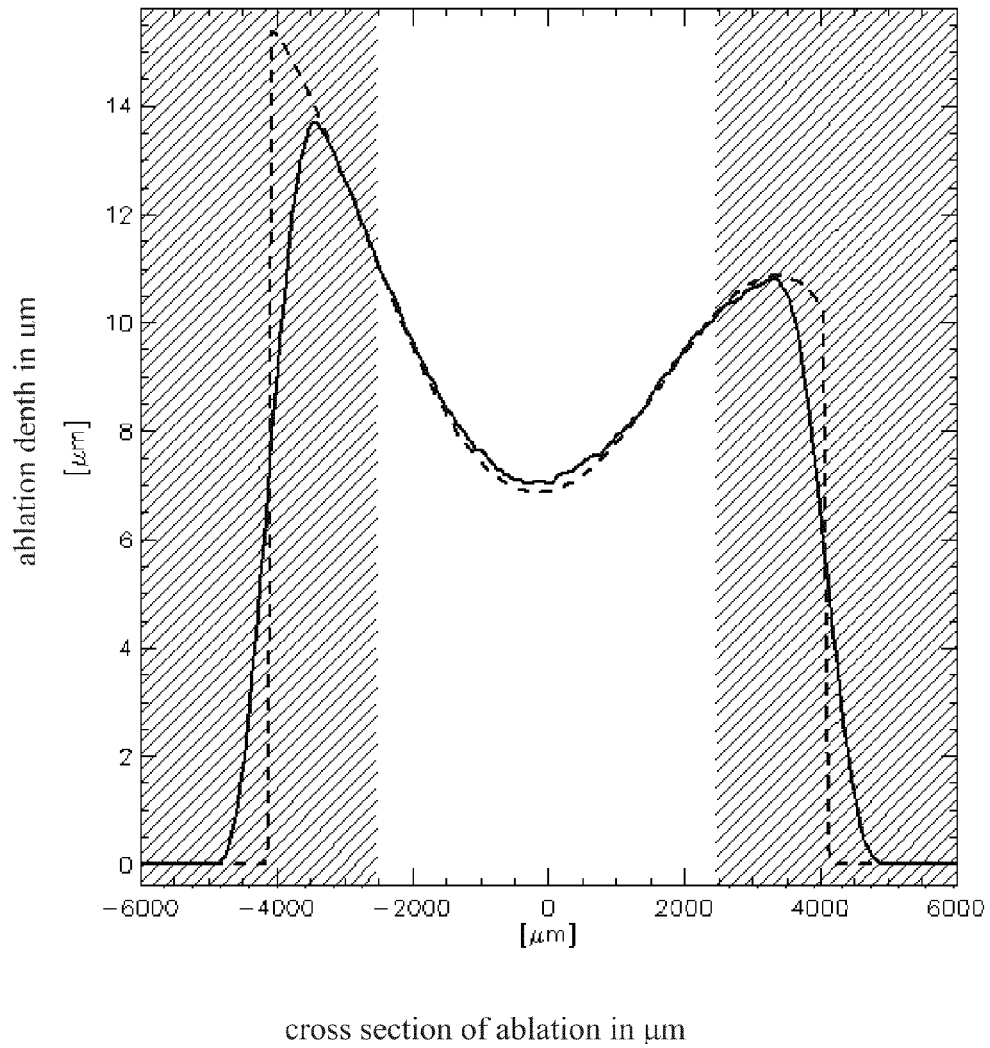
FIG. 5 illustrates a cross section of a simulated ablation profile with the pulse of FIG. 2 in y direction after a $1^{st}$ iteration step.
Figure 6:
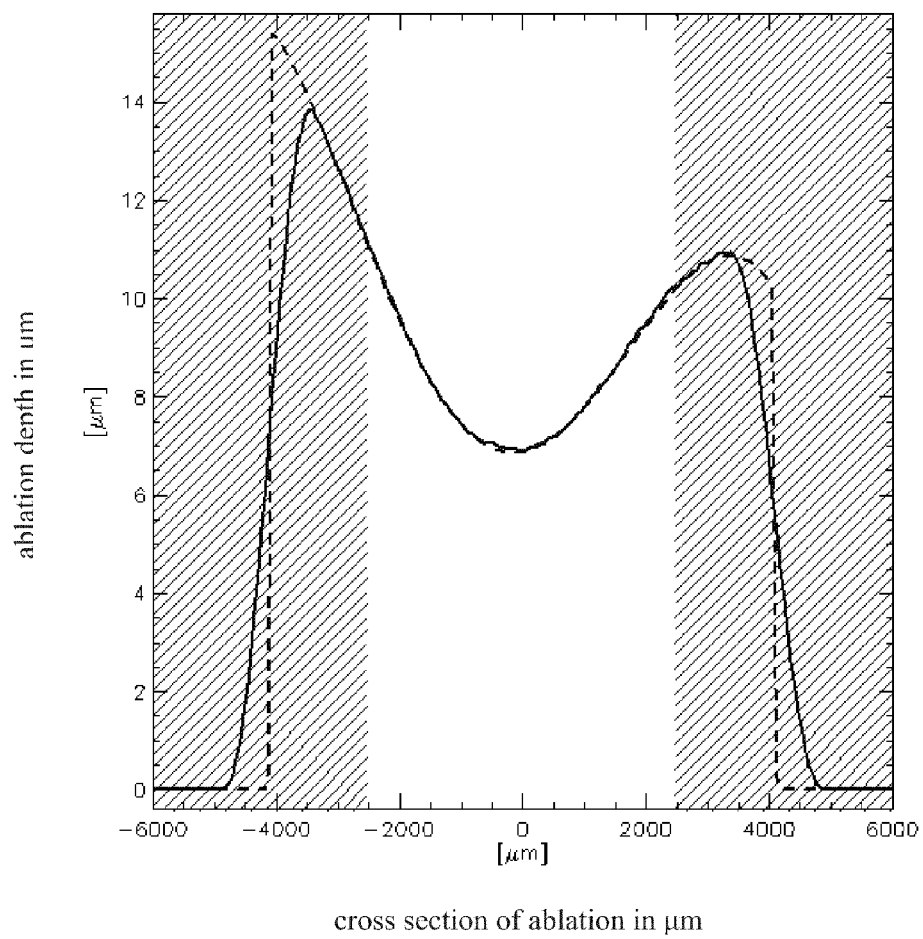
FIG. 6 illustrates the simulated ablation profile of FIG. 5 after a $2^{nd}$ iteration step.

Corresponding to FIGS. 3 and 4, which show the result of the simulated ablation profile relative to the desired ablation profile in x direction, FIGS. 5 and 6 show the approximation of the simulated ablation profile in y direction. The x-axis in FIGS. 5 and 6 relates to the y direction of the cross section of the ablation and the y-axis relates to the ablation depth.

The table of FIG. 7 illustrates the residual wavefronts in amplitudes of Zernike coefficients after the $1^{st}$ iteration and the $2^{nd}$ iteration. Comparing the amplitudes of, e.g., the Zernike coefficient Z110 from FIG. 1 Z110=0.512 with the first iteration Z110=0.112 and the second iteration Z110=−0.004 shows the performance of the approximation of the simulated wavefront to the desired wavefront according to the invention.

FIG. 8 shows a sectional view of a single laser shot ablation, whereas the laser pulse has a 1.6 mm diameter. The single laser shot ablation illustrated in FIG. 8 has a larger diameter and is less deep in comparison with that of FIG. 2. As in FIG. 2, the ablation depth (y-axis) is shown along a central cross section of the laser pulse. In this example, in the center of the laser pulse which is indicated as 0 µm on the x-axis there is a maximal ablation depth of about 0.175 µm.

The approximation as shown in FIGS. 9 to 12 is based on the wavefront as given in FIG. 1, i.e., the desired wavefront (dashed lines) in FIGS. 9 to 12 corresponds to that as illustrated in FIGS. 3 to 6, respectively.

Figure 9:
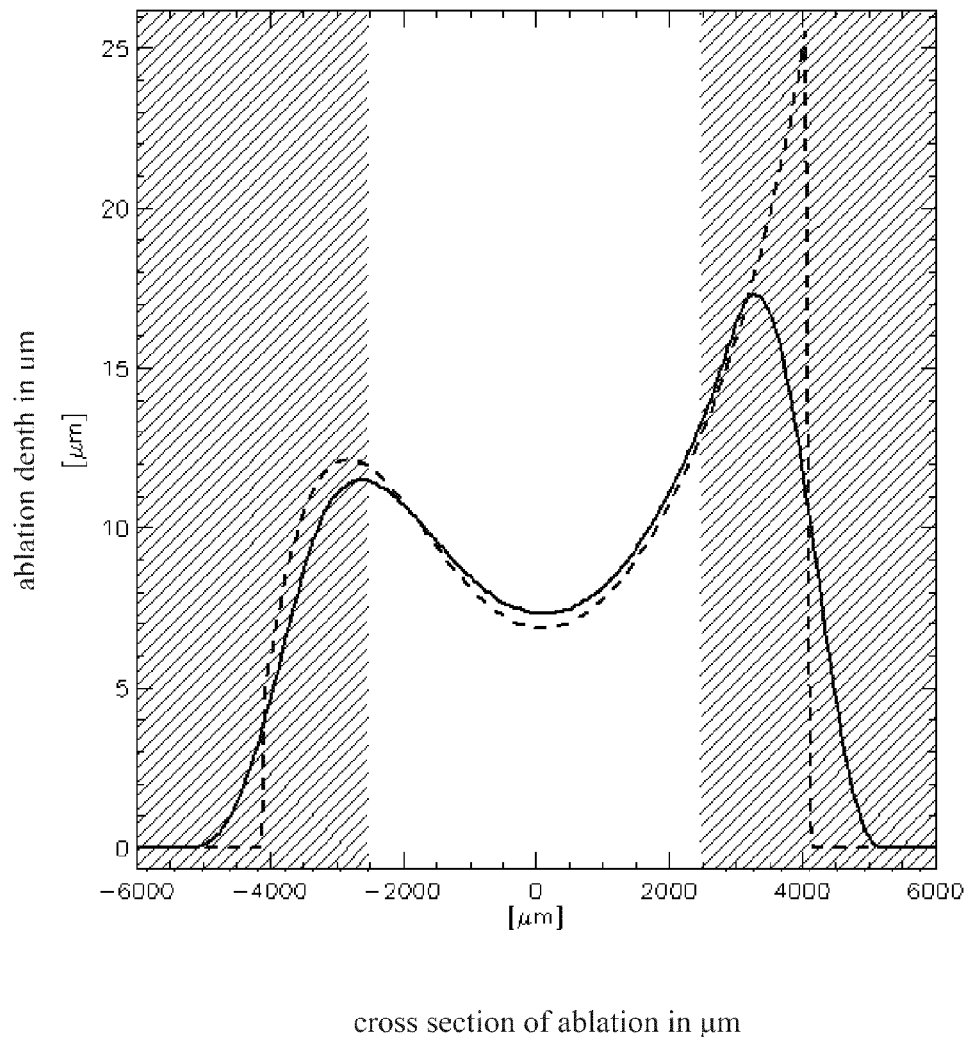
FIG. 9 illustrates a cross section of a simulated ablation profile with the pulse of FIG. 8 in x direction after a $1^{st}$ iteration step.

Corresponding to the foregoing, the simulated ablation profile (continuous line) of FIG. 9 is based on a first series of laser shot positions using information about the pulse characteristics of a single laser shot according to FIG. 8. Upon a comparison of the simulated ablation profile with the desired ablation profile (dashed line) residual structures are determined. The difference between the simulated ablation profile and the desired ablation profile is greater than that according to corresponding FIG. 3 utilizing the laser pulse having a 1.0 mm diameter. Such differences, i.e. the approximation performance, may not only be influenced by laser beam having a different pulse characteristics but also by the utilized dithering algorithm for determining the laser shot positions as well as by the wavefront to be corrected, e.g. having mainly low order aberrations or high order aberrations.

Figure 10:
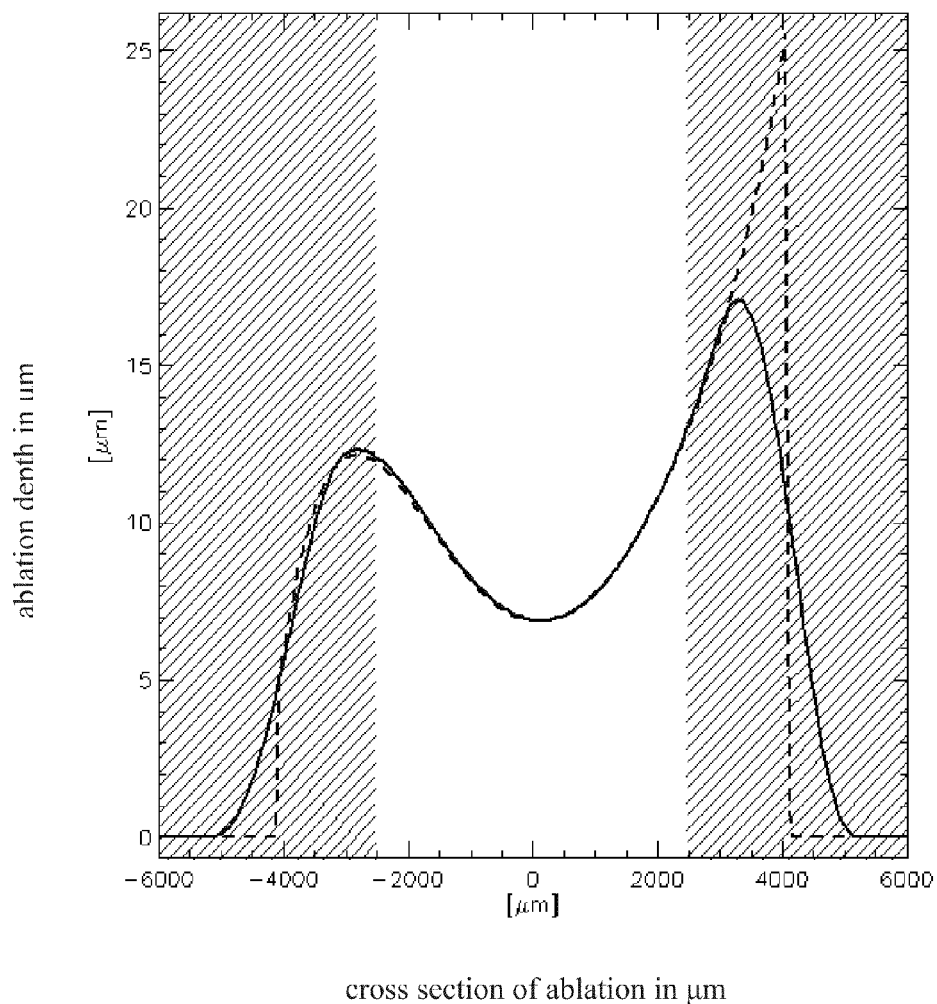
FIG. 10 illustrates the simulated ablation profile of FIG. 9 after a $2^{nd}$ iteration step.
Figure 11:
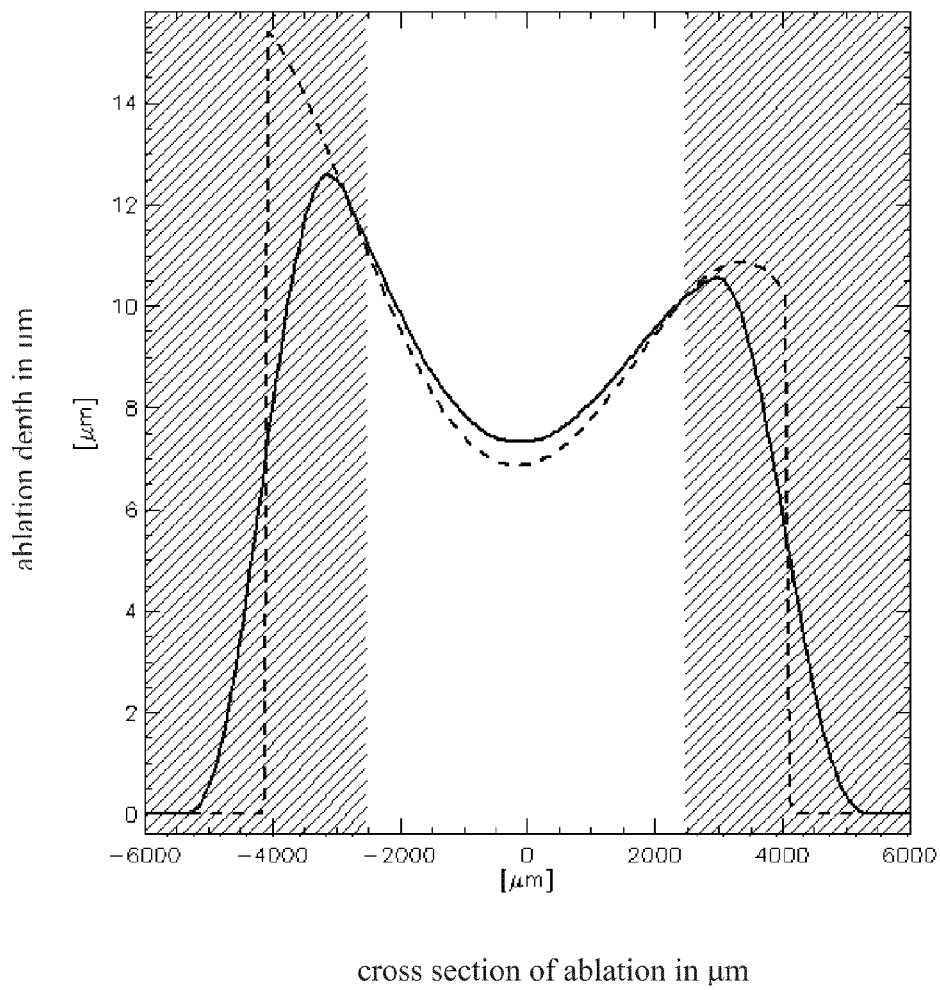
FIG. 11 illustrates a cross section of a simulated ablation profile with the pulse of FIG. 8 in y direction after a $1^{st}$ iteration step.
Figure 12:
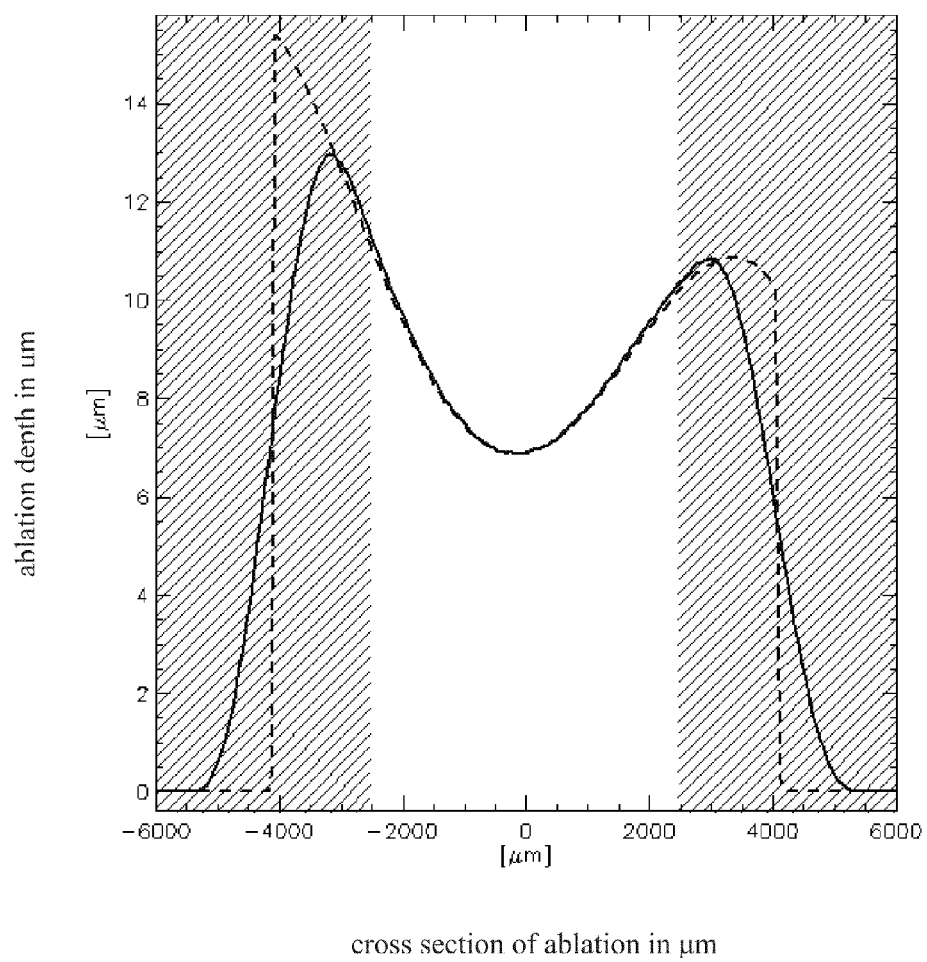
FIG. 12 illustrates the simulated ablation profile of FIG. 11 after a $2^{nd}$ iteration step.
Figure 15:
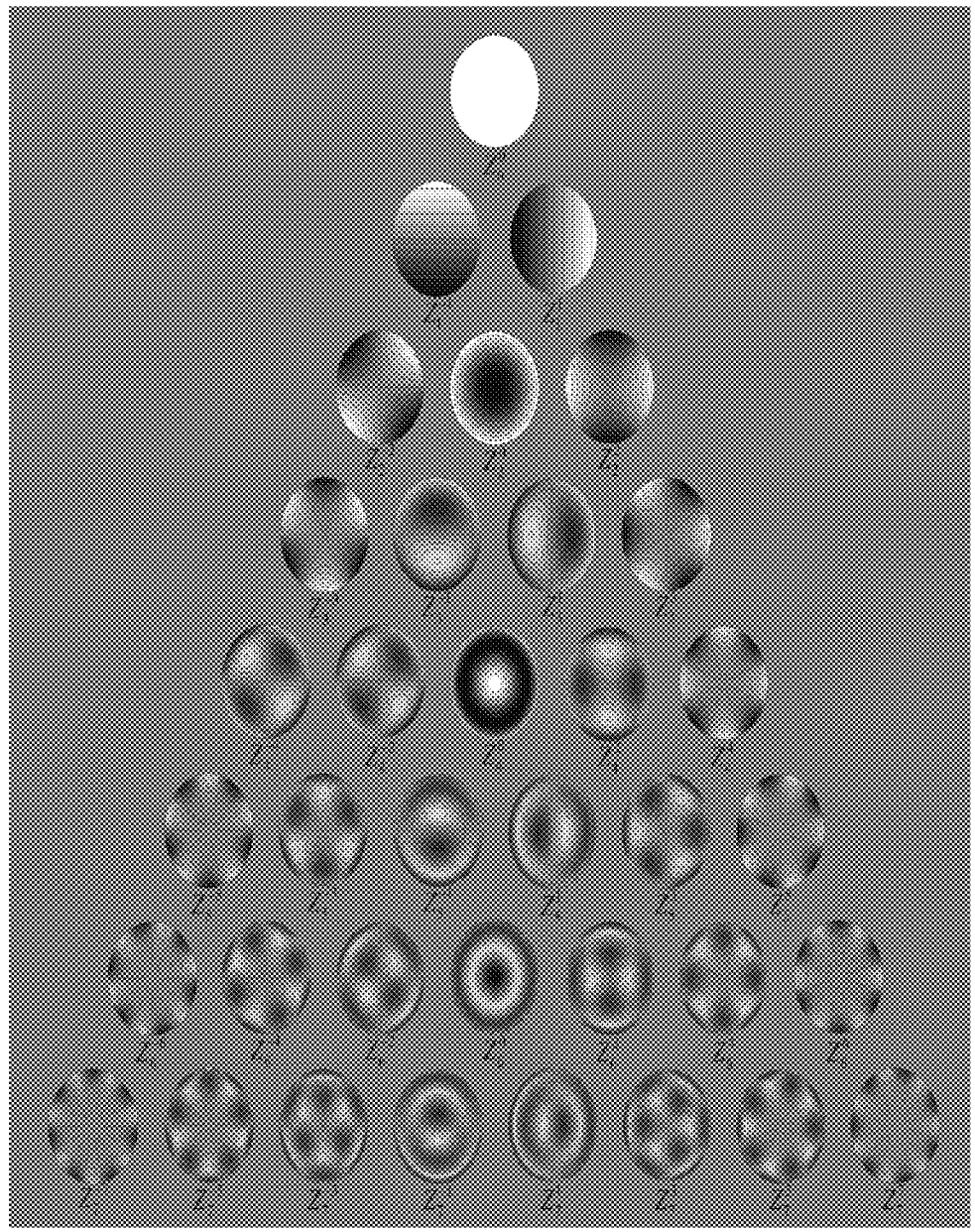
FIG. 15 shows a density plot of the Zernike polynomials up to the seventh order.

FIG. 10 shows the $2^{nd}$ iteration step in x direction corresponding to FIG. 4, and FIGS. 11 and 12 correspond to FIGS. 5 and 6, respectively.

The table of FIG. 13 illustrates the residual wavefronts in amplitudes of Zernike coefficients after the $1^{st}$ iteration and the $2^{nd}$ iteration, corresponding to FIG. 7. Comparing the amplitudes, e.g., the Zernike coefficient Z110 from FIG. 1 Z110=0.512 with the first iteration Z110=0.283 and the second iteration Z110=−0.024 shows that the approximation performance using the laser pulse characteristics according to FIG. 8 is lowered in comparison to that of FIG. 2. As already indicated the performance may depend on at least one of the laser pulse characteristics, the utilized dithering algorithm for determining the laser shot positions and the wavefront to be corrected.

As evident from the summary of the invention, the present invention can be applied to various fields of laser treatments and the figures and the respective description relating to the treatment of an eye is only one example. Preferably this invention provides the base for lasers using large pulse diameters to deliver an ablation profile which is comparable to the results achieved with small spot lasers. The invention is defined by the appended claims and is not limited by the description.

The invention claimed is:

1. A method for providing a laser shot file for use in a laser, the method comprising:
   a) providing information obtained from an eye to be treated,
   b) calculating a desired ablation profile based on information obtained from the eye to be treated,
   c) calculating a first series of laser shot positions based on the desired ablation profile,
   d) generating a first simulated ablation profile using said first series of laser shot positions and using information about pulse characteristics of a single laser shot,
   e) comparing the first simulated ablation profile with the desired ablation profile and determining residual structures, and
   f) calculating a second series of laser shot positions based on the desired ablation profile and the determined residual structures.

2. The method of claim 1 further comprising:
   g) generating a second simulated ablation profile using the second series of laser shot positions and using information about pulse characteristics of a single laser shot,
   h) comparing the second simulated ablation profile with the desired ablation profile and determining further residual structures, and
   i) calculating a further series of laser shot positions based on the desired ablation profile and the determined further residual structures.

3. The method of claim 2, comprising repeating steps f) to g) at least one time, wherein the further series of laser shot positions is used as the second series of laser shot positions.

4. The method of claim 1, wherein the desired ablation profile is calculated based on wavefront information obtained for the eye to be treated, and wherein the wavefront information is preferably given in Zernike coefficients.

5. The method of claim 4, wherein the wavefront information is given as a wavefront of nth-order, and wherein said first series of laser shot positions is calculated based on said nth-order wavefront.

6. The method of claim 5, wherein the difference between the first simulated ablation profile and the desired ablation profile is determined by calculating the difference of a simulated wavefront and a desired wavefront to obtain a residual wavefront, wherein the residual wavefront is described with Zernike coefficients.

7. The method of claim 6, wherein for the following iteration the residual wavefront is added to the previously calculated wavefront.

8. The method of claim 6, wherein the difference between the simulated wavefront and the desired wavefront is filtered to obtain low and/or high spatial frequencies by calculating Zernike coefficients up to the order N', and wherein in each iteration step a respective N'th order of the Zernike coefficients is used, and wherein $$N'=n-2*\text{iteration\_counter},$$

with n being the order of the wavefront information and iteration_counter=number of iteration.

9. The method of claim 8, wherein in each iteration step the corrected wavefront is used for calculating a respective series of laser shot positions, and wherein the iteration steps N' is less than 3.

10. The method of claim 1, further comprising:
controlling a laser apparatus responsive to the provided laser shot file.

11. The method of claim 1, wherein the laser shot file is for use in an excimer laser.

12. The method of claim 1 wherein the laser and the laser shot file are configured for producing a customized contact lens or an intraocular lens.

13. The method of claim 1 wherein the laser and the laser shot file are configured for performing a refractive laser treatment of the eye.

* * * * *